(12) United States Patent
Karasawa

(10) Patent No.: US 7,333,700 B2
(45) Date of Patent: Feb. 19, 2008

(54) SCANNING APPARATUS AND ENDOSCOPE

(75) Inventor: Satoshi Karasawa, Saitama (JP)

(73) Assignees: University of Washington, Seattle, WA (US); PENTAX Corporation, Tokyo (JP)

( * ) Notice: Subject to any disclaimer, the term of this patent is extended or adjusted under 35 U.S.C. 154(b) by 0 days.

(21) Appl. No.: 11/421,629

(22) Filed: Jun. 1, 2006

(65) Prior Publication Data

US 2007/0280614 A1 Dec. 6, 2007

(51) Int. Cl.
*G02B 6/06* (2006.01)
(52) U.S. Cl. ............ 385/117; 385/115; 385/116; 385/123
(58) Field of Classification Search ........ 385/116–118, 385/123, 130, 147; 362/574
See application file for complete search history.

(56) References Cited

U.S. PATENT DOCUMENTS

2001/0055462 A1* 12/2001 Seibel .................... 385/147
2003/0216618 A1* 11/2003 Arai ....................... 600/178
2006/0036132 A1*  2/2006 Renner et al. ........... 600/160

OTHER PUBLICATIONS

Johnston et al., "1.6 mm Diameter Scanning Fiber Endoscope," Submitted to the Optical Society Of America's Frontier in Optics, Tucson, AZ, Oct. 16-20, 2005.
Johnston et al., "Scanning fiber endoscope prototype performance," Accepted for oral presentation on Oct. 13, 2004 (2:00-2:25 pm) in session: Current Trends in Biomedical Spectroscopy and Imaging: Instrumentation (No. FWM2) as part of the Frontiers In Optics 2004, Rochester, NY (optical Society of America).
U.S. Appl. No. 11/427,219, filed Jun. 28, 2006.
U.S. Appl. No. 11/464,319, filed Aug. 14, 2006.

* cited by examiner

*Primary Examiner*—Brian Healy
*Assistant Examiner*—Hung Lam
(74) *Attorney, Agent, or Firm*—Greenblum & Bernstein, P.L.C.

(57) ABSTRACT

An endoscope includes a generally cylindrical optical waveguide, an light source emitting a laser beam, and a generally annular photodiode. The optical waveguide is provided at the distal end of the endoscope. The light source is on or near the center axis of the optical waveguide for emitting a laser beam onto a subject, so that light reflected from the subject enters an annular front-end surface of the optical waveguide. The photodiode faces an annular rear-end surface of the optical waveguide. A waterproof covering tube covers the optical waveguide and the photodiode.

26 Claims, 4 Drawing Sheets

SCANNING APPARATUS AND ENDOSCOPE

BACKGROUND OF THE INVENTION

1. Field of the Invention

The present invention relates to a scanning apparatus, and more particularly, to a scanning fiber endoscope, in which a fiber scanner is provided so that a focused laser spot is scanned over a subject, such as tissue to be observed, to detect an image of the subject.

2. Description of the Related Art

Recently, a scanning fiber endoscope has been proposed, which has an annular photodiode on a front surface of the objective lens unit, and a fiber scanner disposed behind the objective lens unit. Namely, a laser spot emitted from the fiber scanner is output through the objective lens unit to hit a surface of the subject, and is reflected off of the subject to enter the photodiode. However, in a scanning fiber endoscope the distal end should be waterproofed, which is very difficult, and has not been accomplished so far.

SUMMARY OF THE INVENTION

Therefore, an object of the present invention is to provide an endoscope including a scanning fiber endoscope, in which the distal end can be easily waterproofed.

According to one aspect of the present invention, there is provided a scanning fiber endoscope including an optical waveguide having a generally cylindrical shape and located at a distal end of the endoscope, the optical waveguide having a generally annular front-end surface and a generally annular rear-end surface; a fiber scanner having an optical fiber positioned on or adjacent to a center axis of the optical waveguide, and configured to vibrate in resonance for scanning a focused laser spot over a subject, so that light reflected from the subject enters the annular front-end surface of the optical waveguide; a photodiode having a generally annular shape and located adjacent to and facing the annular rear-end surface of the optical waveguide; and a covering tube that covers the optical waveguide and the photodiode.

The optical waveguide may include a generally flat core sandwiched between generally flat claddings, to form a multi-layer optical waveguide structure. The multi-layer optical waveguide structure may be configured as a hollow cylinder.

The optical waveguide may be configured as a hollow cylinder. The fiber scanner may be positioned within the hollow cylinder. The endoscope may further include an objective optical system positioned within the hollow cylinder. The objective optical system may be located at the distal end of the endoscope and adjacent to the fiber scanner. The objective optical system has a first numerical aperture, the optical waveguide has a second numerical aperture, and the second numerical aperture is larger than the first numerical aperture.

The endoscope may further include a base formed of insulating material, the base having a generally annular support portion on which the photodiode is mounted.

The endoscope may further include a generally cylindrical support member around which the optical waveguide is located, and an insulator located between the generally cylindrical support member and the fiber scanner. The insulator may include a generally disk-shaped insulator fixed to a rear-end portion of the support member, and having a center hole into which the fiber scanner is fitted. The covering tube may include a waterproof material.

According to a further aspect of the present invention, there is provided an endoscope including an optical waveguide having a generally cylindrical shape and located at a distal end of the endoscope, the optical waveguide having a generally annular front-end surface and a generally annular rear-end surface; a light source positioned on or adjacent to a center axis of the optical waveguide to emit a laser beam onto a subject, so that light reflected from the subject enters the annular front-end surface of the optical waveguide, a photodiode having a generally annular shape and located adjacent to and facing the annular rear-end surface of the optical waveguide; and a covering tube that covers the optical waveguide and the photodiode.

According to a further aspect of the present invention, there is provided a scanning apparatus including an optical waveguide having a generally cylindrical shape, the optical waveguide having a generally annular front-end surface and a generally annular rear-end surface; a fiber scanner having an optical fiber positioned on or adjacent to a center axis of the optical waveguide, and configured to vibrate in resonance for scanning a focused laser spot over a subject, so that light reflected from the subject enters the annular front-end surface of the optical waveguide; a photodiode having a generally annular shape and located adjacent to and facing the annular rear-end surface of the optical waveguide; and a covering tube that covers the optical waveguide and the photodiode.

The optical waveguide may include a generally flat core sandwiched between generally flat claddings, to form a multi-layer optical waveguide structure. The multi-layer optical waveguide structure may be configured as a hollow cylinder.

The optical waveguide may be configured as a hollow cylinder. The fiber scanner may be positioned within the hollow cylinder. The scanning apparatus may further include an objective optical system positioned within the hollow cylinder. The objective optical system may be located adjacent to the fiber scanner. The objective optical system has a first numerical aperture, the optical waveguide has a second numerical aperture, and the second numerical aperture is larger than the first numerical aperture.

The scanning apparatus may further include a base formed of insulating material, the base having a generally annular support portion on which the photodiode is mounted.

The scanning apparatus may further include a generally cylindrical support member around which the optical waveguide is located, and an insulator located between the generally cylindrical support member and the fiber scanner. The insulator may include a generally disk-shaped insulator fixed to a rear-end portion of the support member, and having a center hole into which the fiber scanner is fitted. The covering tube may include a waterproof material.

According to a further aspect of the present invention, there is provided an apparatus including an optical waveguide having a generally cylindrical shape, the optical waveguide having a generally annular front-end surface and a generally annular rear-end surface; a light source positioned on or adjacent to a center axis of the optical waveguide to emit a laser beam onto a subject, so that light reflected from the subject enters the annular front-end surface of the optical waveguide; a photodiode having a generally annular shape and located adjacent to and facing the annular rear-end surface of the optical waveguide; and a covering tube that covers the optical waveguide and the photodiode.

The foregoing and other objects, features, aspects and advantages of the present invention will become more apparent from the following detailed description of the present invention when taken in conjunction with the accompanying drawings.

BRIEF DESCRIPTION OF THE DRAWINGS

The present invention is further described in the detail description which follows, in reference to the noted plurality of drawings, by way of non-limiting examples of preferred embodiments of the present invention, in which like characters represent like elements throughout the several views of the drawings, and wherein.

DETAILED DESCRIPTION

Figure 1:
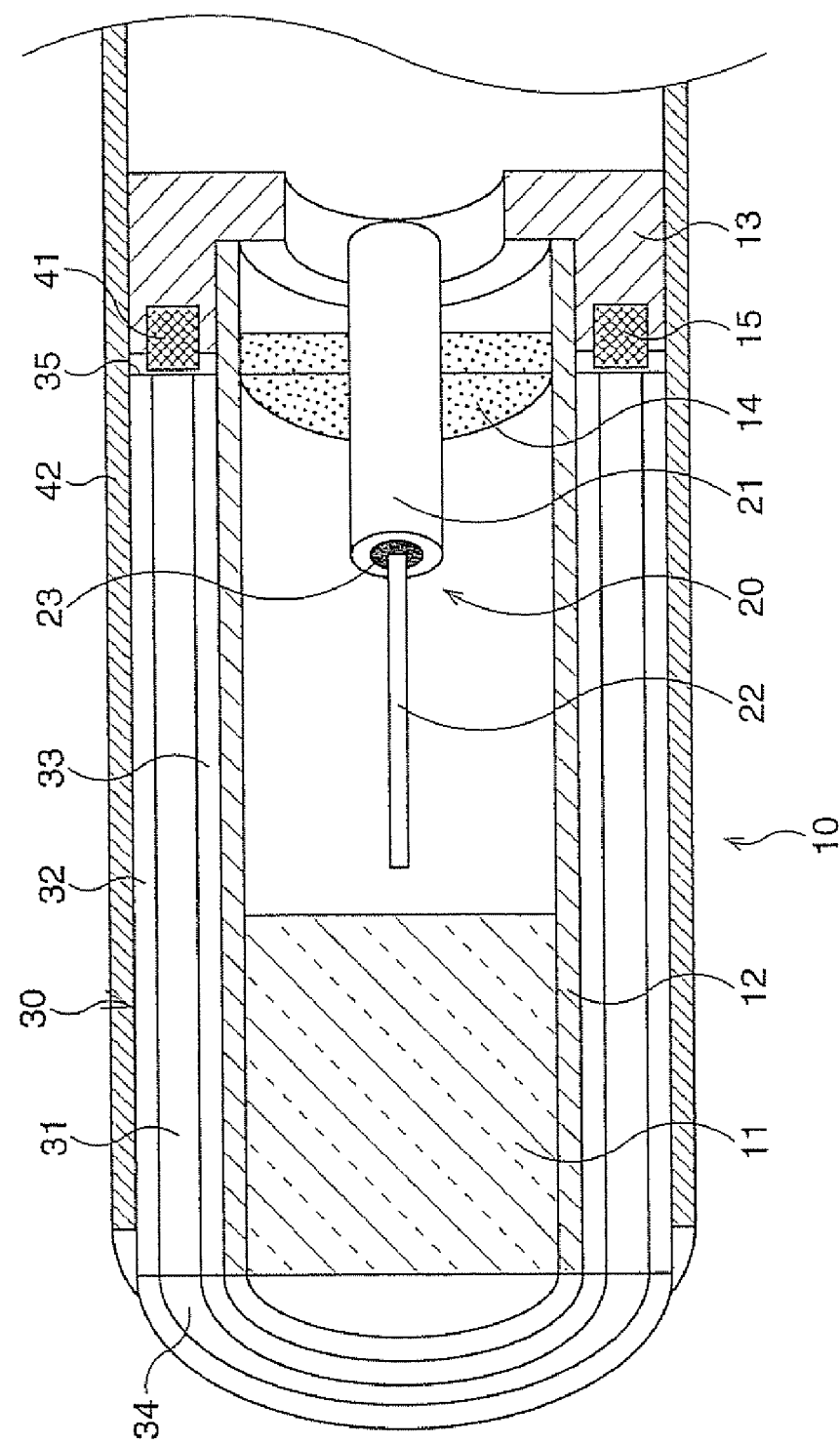
FIG. 1 is a perspective view, in which a scanning fiber endoscope of an embodiment of the present invention is cut by a plane passing through the center axis of the scanning fiber endoscope.

The present invention will be described below with reference to the embodiments shown in the drawings.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIG. 1 shows the distal end 10 of a scanning fiber endoscope (or scanning apparatus) of an embodiment of the present invention. An objective lens unit (or objective optical system) 11 is fit in an inner wall of a front-end portion of a cylindrical support member 12. The support member 12 can be made of any suitable material.

A base 13 is fit or fixed on a rear-end portion of the support member 12. The base 13 can also be formed integrally with the rear-end portion of the support member 12. The base 13 can be made of any suitable material, such as a suitable insulating material.

A fiber scanner 20 is disposed close to the rear-end portion of the support member 12. The fiber scanner 20 is fit in a center hole formed in a generally disk-shaped insulator 14, which is inserted in and fixed to the rear-end portion of the support member 12. Thus, the fiber scanner 20 is located on or adjacent to the center axis of the support member 12. Further, the disk-shaped insulator 14 can be connected to the rear-end portion of the support member 12 by in any suitable manner, such as by a suitable fixing material, such as an adhesive. Alternatively, a groove or recess may be provided on an inner surface of the rear-end portion of the support member 12 to fix the disk-shaped insulator 14. Further, the disk-shaped insulator 14 may be slightly larger in diameter that the inside of the rear-end portion of the support member 12 in order to provide an interference fit between the disk-shaped insulator 14 and support member 12.

The fiber scanner 20 has a tube 21, and a single mode optical fiber 22, the tip of which faces the objective lens unit 11. The tube 21 and the optical fiber 22 may be attached in any suitable manner, such as by a suitable attaching material, such as an adhesive 23 or glass material. A laser beam is output from the tip of the optical fiber 22, and emitted to the outside through the objective lens unit 11. The optical fiber 22 is supported at an end by the tube 21, and vibrated in any suitable manner in order to perform scanning. For example, the tube 21 may be made of piezoelectric material and for driving the optical fiber 22. The optical fiber 22 is vibrated in resonance through the tube 21 to scan a focused laser spot over a subject to be observed by the endoscope.

An optical waveguide 30 is of a generally planar type, in which a flat core 31 is sandwiched by two generally flat claddings 32 and 33, which have smaller refractive index than that of the flat core 31, to form a three-layer optical waveguide structure. This optical waveguide structure is formed into a hollow cylindrical shape. The core 31 and claddings 32, 33 can be made of any suitable material. The optical waveguide 30 is arranged about an outer surface of the support member 12, and may be fitted thereon. The optical waveguide 30 has an annular front-end surface 34 and an annular rear-end surface 35. The rear-end surface 35 is close to the base 13. A photodiode 41 is formed in an annular, ring shape, and is mounted on an annular support portion 15 of the base 13 so as to face the rear-end surface 35 of the optical waveguide 30.

Alternatively, it should be appreciated that instead of the flat core 31 being sandwiched by the flat claddings 32 and 33, the core 31 may be provided with a thin coating or film layer. In this regard, the thin layers may be formed of any suitable material having a suitable refractive index. Also, the thin layers may be deposited directly on respective surfaces of the core 31. Further, the thin layers may be formed directly on the support member 12 and a covering tube 42.

The photodiode 41 may have a relatively simple structure, and the cost and the sensitivity may be relatively low in comparison with the high-sensitivity photodiode provided in conventional endoscopes. A high-sensitivity photodiode, having a complicated structure, may be provided in a processor to which the endoscope is connected, so that image processing is performed on the image obtained by the endoscope.

The covering tube 42 can provide a waterproof cover for the optical waveguide 30, the photodiode 41, and the base 13. Thus, the distal end 10 of the endoscope is completely waterproofed. The covering tube can be made of any suitable material.

Figure 2:
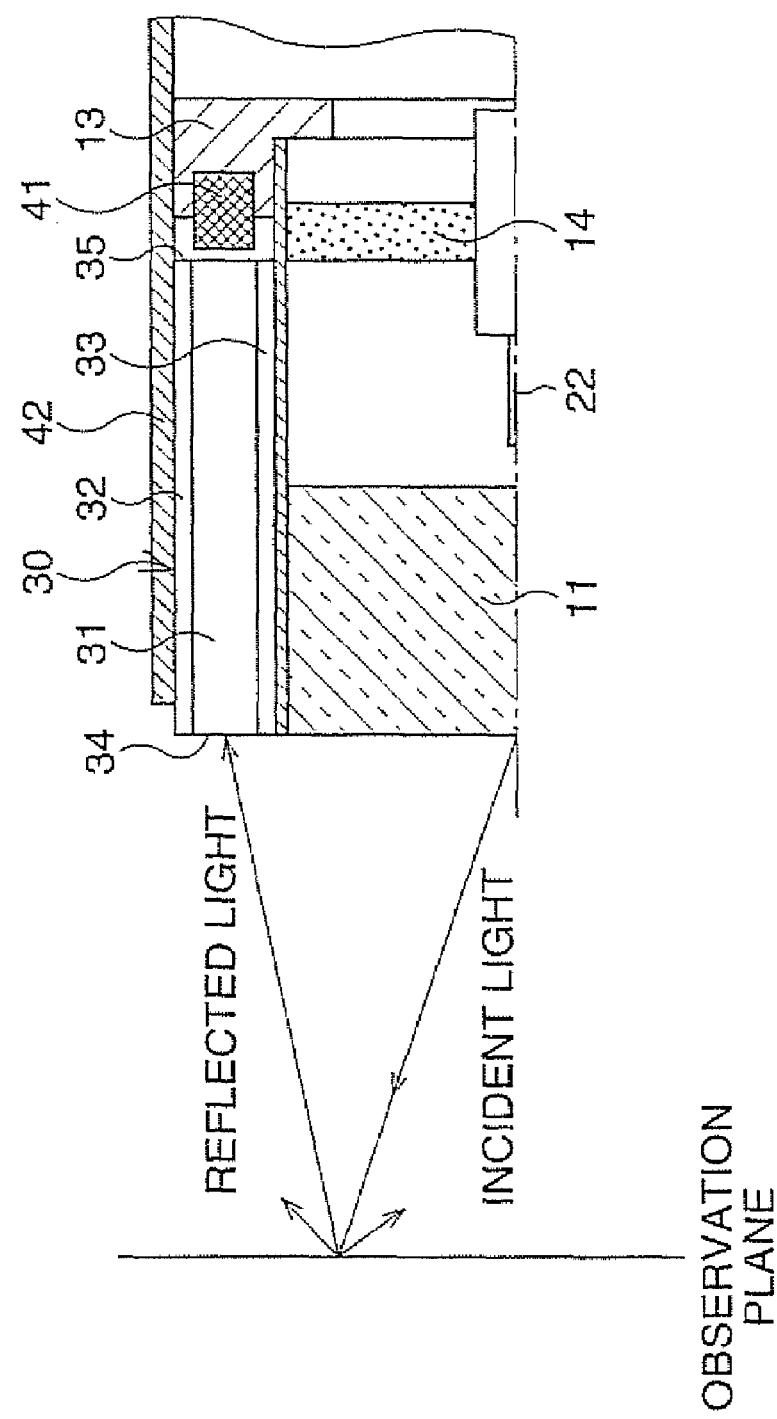
FIG. 2 is a view showing a relationship between an emergent laser beam and a reflected laser beam.

The optical fiber 22 is positioned on or adjacent to the center axis of the cylindrical shape of the optical waveguide 30. Thus, as shown in FIG. 2, when the fiber scanner 20 is actuated, the optical fiber 21 is vibrated in resonance, so that a laser beam (i.e., incident light) emerges through the center of the objective lens unit 11, which is disposed in a front end of the optical waveguide 30, and is scanned over a subject. For example, the laser beam can be spirally scanner over a subject. The laser beam is reflected off of the subject, and the reflected light enters the annular front-end surface 34 of the optical waveguide 30. The laser beam proceeds through the core 31, while reflecting off of the claddings 32 and 33, and is received by the photodiode 41. In this manner, a pixel signal is generated by the photodiode 41, and can be transmitted through a suitable connection, such as an electrical wire, to a processor.

Figure 3:
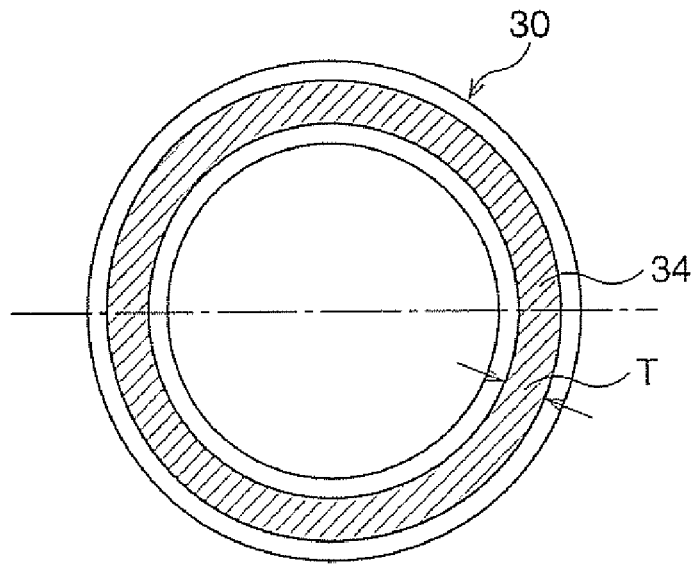
FIG. 3 is a front view of an optical waveguide provided in the endoscope of the embodiment.
Figure 4:
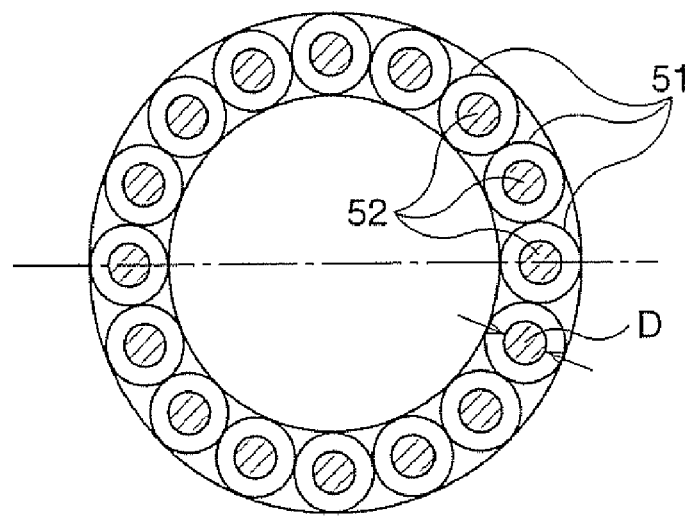
FIG. 4 is a front view of an optical waveguide provided in an endoscope of a prior art.

FIG. 3 shows a front view of the planar type optical waveguide 30 as described above. FIG. 4 shows a front view of a conventional optical waveguide, in which a plurality of optical fibers 51 having cores 52 are arranged in a circle. In FIGS. 3 and 4, the thickness T of the core 34 is depicted as identical with the diameter D of the core 52. As can be seen in a comparison between FIGS. 3 and 4, the area of the light-receiving surface of the core 34 is much larger than the total area of the cores 52 of the plurality of multi-mode optical fibers 51. Therefore, according to an embodiment of the present invention, since a sufficient amount of light is received through the optical waveguide 30, a clearer image can be obtained even when a low-sensitivity, low-cost photodiode 41 is provided.

Figure 5:
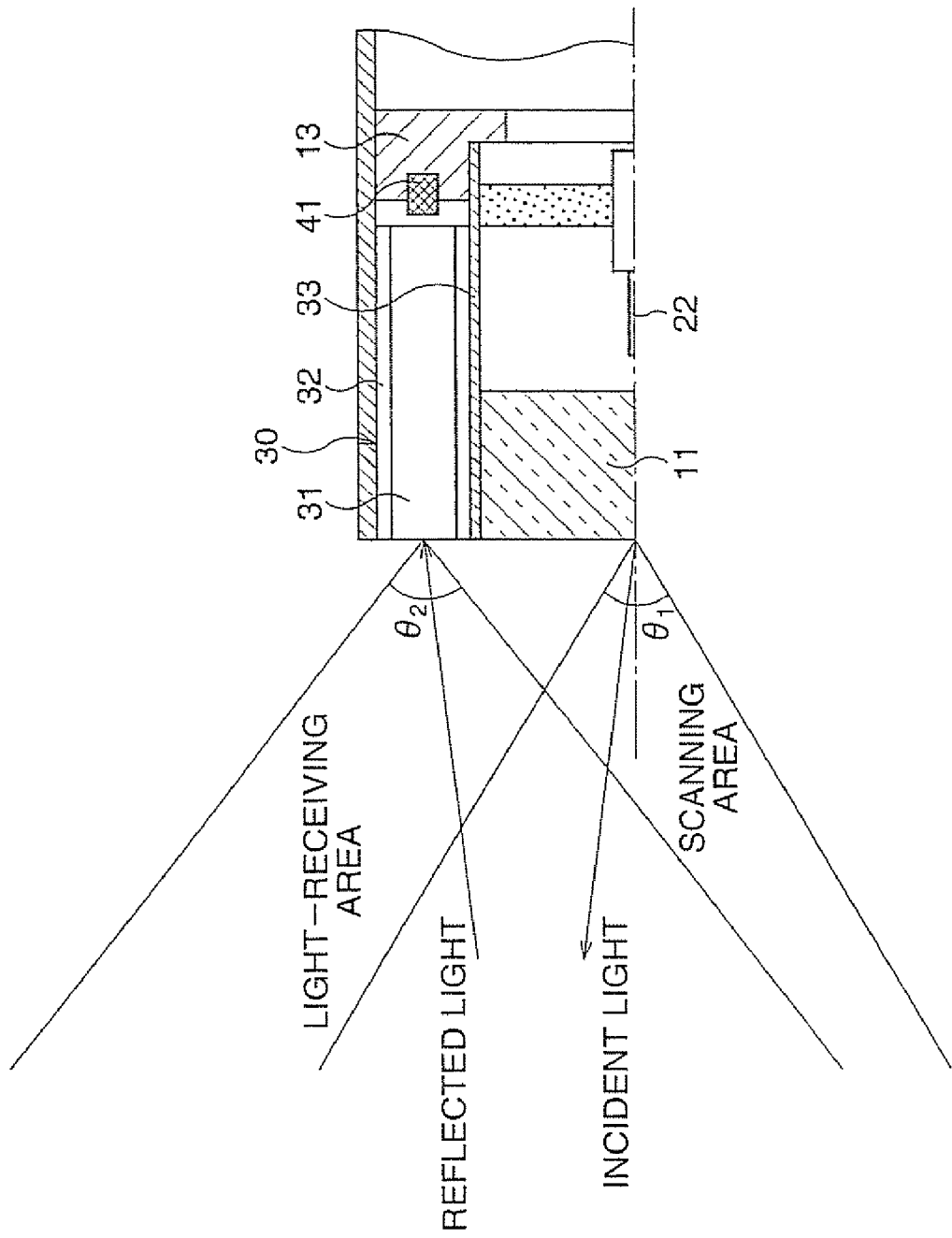
FIG. 5 is a view showing a relationship between a scanning area and a light-receiving area.

With reference to FIG. 5, a numerical aperture (NA) of the optical waveguide 30 is described below. The objective lens unit 11 has a first NA, and the optical waveguide 30 has a second NA, which is larger than the first NA. Namely, a second angle $\theta_2$, by which the laser beam reflected by the subject can enter the optical waveguide 30, is larger than a first angle $\theta_1$, by which the laser beam emitted through the objective lens unit 11 can be diverged. In other words, the light-receiving area is wider than the scanning area, so that the reflected light is received by the optical waveguide 30 with a high efficiency.

Thus, due to the large NA of the optical waveguide 30, the photodiode 41 does not need to have a high sensitivity. Further, due to the large NA together with the planar optical waveguide 30, the photodiode 41 can receive more of the reflected light, so that a clearer image can be sensed by the photodiode 41, and thus, the cost of the endoscope can be drastically reduced.

Note that the present invention can also be applied to a non-scanning endoscope that does not include a fiber scanner which vibrates in resonance for scanning a focused laser spot over a subject. The present invention can also be implemented in other applications, such as microscopy and confocal microscopy.

Although the embodiments of the present invention have been described herein with reference to the accompanying drawings, obviously many modifications and changes may be made by those skilled in the art without departing from the scope of the invention.

It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The above disclosed subject matter is to be considered illustrative, and not restrictive, and the appended claims are intended to cover all such modifications, enhancements, and other embodiments which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

Although the invention has been described with reference to several exemplary embodiments, it is understood that the words that have been used are words of description and illustration, rather than words of limitation. As the present invention may be embodied in several forms without departing from the spirit or essential characteristics thereof, it should also be understood that the above-described embodiments are not limited by any of the details of the foregoing description, unless otherwise specified. Rather, the above-described embodiments should be construed broadly within the spirit and scope of the present invention as defined in the appended claims. Therefore, changes may be made within the metes and bounds of the appended claims, as presently stated and as amended, without departing from the scope and spirit of the invention in its aspects.

What is claimed is:

1. A scanning fiber endoscope, comprising:
    an optical waveguide having a generally cylindrical shape and located at a distal end of the endoscope, said optical waveguide having a generally annular front-end surface and a generally annular rear-end surface;
    a fiber scanner having an optical fiber positioned on or adjacent to a center axis of said optical waveguide, and configured to vibrate in resonance for scanning a focused laser spot over a subject, so that light reflected from the subject enters the annular front-end surface of said optical waveguide;
    a photodiode having a generally annular shape, said photodiode located adjacent to and facing the annular rear-end surface of said optical waveguide, said photodiode being configured to receive light reflected from the subject through said optical waveguide; and
    a covering tube that covers said optical waveguide and said photodiode.

2. The scanning fiber endoscope according to claim 1, wherein said optical waveguide includes a single generally flat core sandwiched between generally flat claddings, to form a multi-layer optical waveguide structure.

3. The scanning fiber endoscope according to claim 2, wherein the multi-layer optical waveguide structure is configured as a hollow cylinder.

4. The scanning fiber endoscope according to claim 1, wherein said optical waveguide is configured as a hollow cylinder.

5. The scanning fiber endoscope according to claim 4, wherein said fiber scanner is positioned within the hollow cylinder.

6. The scanning fiber endoscope according to claim 4, further comprising an objective optical system positioned within the hollow cylinder.

7. The scanning fiber endoscope according to claim 1, further comprising an objective optical system located at the distal end of the endoscope and adjacent to said generally annular front-end surface of said optical waveguide.

8. The scanning fiber endoscope according to claim 7, wherein said objective optical system has a first numerical aperture, said optical waveguide has a second numerical aperture, and the second numerical aperture is larger than the first numerical aperture.

9. The scanning fiber endoscope according to claim 1, further comprising a base formed of insulating material, said base having a generally annular support portion on which said photodiode is mounted.

10. The scanning fiber endoscope according to claim 1, further comprising a generally cylindrical support member around which said optical waveguide is located, and an insulator located between said generally cylindrical support member and said fiber scanner.

11. The scanning fiber endoscope according to claim 10, wherein said insulator comprises a generally disk-shaped insulator fixed to a rear-end portion of the support member, and having a center hole into which said fiber scanner is fitted.

12. The scanning fiber endoscope according to claim 1, wherein said covering tube comprises a waterproof material.

13. An endoscope comprising:
   an optical waveguide having a generally cylindrical shape and located at a distal end of the endoscope, said optical waveguide having a generally annular front-end surface and a generally annular rear-end surface;
   a light source positioned on or adjacent to a center axis of said optical waveguide to emit a laser beam onto a subject, so that light reflected from the subject enters the annular front-end surface of said optical waveguide;
   a photodiode having a generally annular shape, said photodiode located adjacent to and facing the annular rear-end surface of said optical waveguide, said photodiode being configured to receive light reflected from the subject through said optical waveguide; and
   a covering tube that covers said optical waveguide and said photodiode.

14. A scanning apparatus, comprising:
   an optical waveguide having a generally cylindrical shape, said optical waveguide having a generally annular front-end surface and a generally annular rear-end surface;
   a fiber scanner having an optical fiber positioned on or adjacent to a center axis of said optical waveguide, and configured to vibrate in resonance for scanning a focused laser spot over a subject, so that light reflected from the subject enters the annular front-end surface of said optical waveguide;
   a photodiode having a generally annular shape, said photodiode located adjacent to and facing the annular rear-end surface of said optical waveguide, said photodiode being configured to receive light reflected from the subject through said optical waveguide; and
   a covering tube that covers said optical waveguide and said photodiode.

15. The scanning apparatus according to claim 14, wherein said optical waveguide includes a single generally flat core sandwiched between generally flat claddings, to form a multi-layer optical waveguide structure.

16. The scanning apparatus according to claim 15, wherein the multi-layer optical waveguide structure is configured as a hollow cylinder.

17. The scanning apparatus according to claim 14, wherein said optical waveguide is configured as a hollow cylinder.

18. The scanning apparatus according to claim 17, wherein said fiber scanner is positioned within the hollow cylinder.

19. The scanning apparatus according to claim 17, further comprising an objective optical system positioned within the hollow cylinder.

20. The scanning apparatus according to claim 14, further comprising an objective optical system located adjacent to said generally annular front-end surface of said optical waveguide.

21. The scanning apparatus according to claim 20, wherein said objective optical system has a first numerical aperture, said optical waveguide has a second numerical aperture, and the second numerical aperture is larger than the first numerical aperture.

22. The scanning apparatus according to claim 14, further comprising a base formed of insulating material, said base having a generally annular support portion on which said photodiode is mounted.

23. The scanning apparatus according to claim 14, further comprising a generally cylindrical support member around which said optical waveguide is located, and an insulator located between said generally cylindrical support member and said fiber scanner.

24. The scanning apparatus according to claim 23, wherein said insulator comprises a generally disk-shaped insulator fixed to a rear-end portion of the support member, and having a center hole into which said fiber scanner is fitted.

25. The scanning apparatus according to claim 14, wherein said covering tube comprises a waterproof material.

26. An apparatus comprising:
   an optical waveguide having a generally cylindrical shape, said optical waveguide having a generally annular front-end surface and a generally annular rear-end surface;
   a light source positioned on or adjacent to a center axis of said optical waveguide to emit a laser beam onto a subject, so that light reflected from the subject enters the annular front-end surface of said optical waveguide;
   a photodiode having a generally annular shape, said photodiode located adjacent to and facing the annular rear-end surface of said optical waveguide, said photodiode being configured to receive light reflected from the subject through said optical waveguide; and
   a covering tube that covers said optical waveguide and said photodiode.

* * * * *